United States Patent
Caldararo et al.

(10) Patent No.: US 7,982,052 B2
(45) Date of Patent: *Jul. 19, 2011

(54) PROCESS FOR THE PREPARATION OF STABLE NITROXYL RADICALS

(75) Inventors: Maria Caldararo, Trecate-novara (IT); Riccardo Po', Livorno (IT); Marco Ricci, Novara (IT)

(73) Assignee: Polimeri Europa S.p.A., San Donato Milanese (IT)

( * ) Notice: Subject to any disclaimer, the term of this patent is extended or adjusted under 35 U.S.C. 154(b) by 363 days.

This patent is subject to a terminal disclaimer.

(21) Appl. No.: 12/161,283

(22) PCT Filed: Feb. 9, 2007

(86) PCT No.: PCT/EP2007/001879
§ 371 (c)(1),
(2), (4) Date: Jul. 17, 2008

(87) PCT Pub. No.: WO2007/093452
PCT Pub. Date: Aug. 23, 2007

(65) Prior Publication Data
US 2010/0240909 A1   Sep. 23, 2010

(30) Foreign Application Priority Data

Feb. 16, 2006  (IT) ............... MI2006A0285

(51) Int. Cl.
*C07D 209/44* (2006.01)
(52) U.S. Cl. .................................. 548/482
(58) Field of Classification Search .......... None
See application file for complete search history.

(56) References Cited

U.S. PATENT DOCUMENTS
2007/0015922 A1  1/2007  Caldararo et al.
2007/0282113 A1  12/2007 Caldararo et al.

FOREIGN PATENT DOCUMENTS
WO  2004 078720  9/2004
WO  2006 029697  3/2006

OTHER PUBLICATIONS

Griffiths, Peter G. et al., "Synthesis of the Radical Scavenger 1,1,3,3-Tetramethylisoindolin-2-yloxyl", Australian Journal of Chemistry, vol. 36, No. 2, pp. 397-401, XP 000566821, (1983).

*Primary Examiner* — Kamal A Saeed
(74) *Attorney, Agent, or Firm* — Oblon, Spivak, McClelland, Maier & Neustadt, L.L.P.

(57) ABSTRACT

Process for the preparation of stable nitroxyl radicals (I) starting from N-benzylphthalimide in two steps. In the first step, the intermediate N-benzyl-1,1,3,3-tetra-alkylisoindoline is prepared by treatment with a Grignard reagent, prepared in methyl-tert-butyl ether, of N-benzylphthalimide, obtained in the same reaction environment starting from phthalic anhydride and benzylamine. In the second step, the N-benzyl-1,1,3,3-tetra-alkylisoindoline is transformed into the nitroxyl radical by hydrogenolysis and subsequent oxidation with hydrogen peroxide in the presence of a catalyst selected from acids and salts of polymolybdic or polytungstic acids.

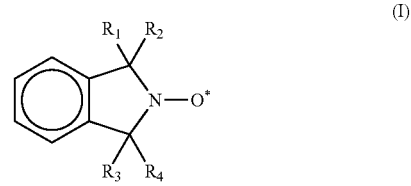

(I)

19 Claims, No Drawings

PROCESS FOR THE PREPARATION OF STABLE NITROXYL RADICALS

The present invention relates to a improved process for the preparation of stable nitroxyl radicals having general formula (I):

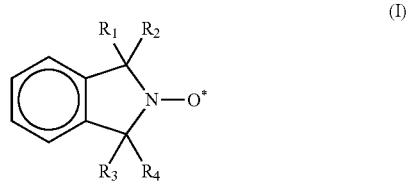

wherein $R_1$, $R_2$, $R_3$ and $R_4$, the same or different, represent alkyl or isoalkyl groups containing from 1 to 8 carbon atoms.

These stable nitroxyl radicals are used as intermediates in the synthesis of more complex molecules or as additives (polymerization inhibitors) or as radical reaction control agents and, in particular, polymerization reactions. For these purposes, they are prepared by oxidation with hydrogen peroxide of the corresponding secondary amines, 1,1,3,3-tetra-alkylisoindolines having formula (II):

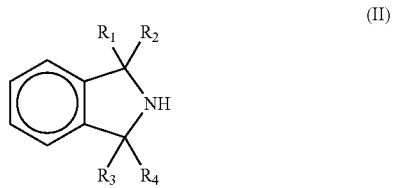

in the presence of catalysts based on tungstates, as described, for example, in P. G. Griffiths, G. Moad, E. Rizzardo, D. H. Solomon, "Australian Journal of Chemistry" 1983, 36, 397.

The 1,1,3,3-tetra-alkylisoindolines having formula (II) can in turn be prepared, for example, by the cyclodimerization of dipropargylamines and acetylenes in the presence of catalysts based on nickel (G. P. Chiusoli, L. Pallini, G. Terenght, "Transition Metal Chemistry" 1983, 8, 189) or cobalt (G. P. Chiusoli, L. Pallini, G. Terenghi, "Transition Metal Chemistry" 1984, 9, 360) or by carbonylation, in the presence of catalysts based on palladium, of dipropargylamines (G. P. Chiusoli, M. Costa, S. Reverberi, G. Salerno, M. G. Terenghi, "Gazzetta Chimica Italiana" 1987, 117, 695). These synthetic methods however are jeopardized by the necessity of preparing the 1,6-diacetylenes (dipropargylamines) used as raw material.

The synthesis set up by Rizzardo and coworkers is of the greatest practical interest, and comprises the synthesis of N-benzylpthalimide from benzyl bromide and potassium phthalimide, followed by its alkylation with a Grignard reagent. In the synthesis of 1,1,3,3-tetramethylisoindoline, for example, the Grignard reagent was prepared starting from methyl iodide and magnesium using, as solvents, ethyl ether and toluene (in succession): after 4 hours at reflux, N-benzyl-1,1,3,3-tetramethylisoindoline is obtained (37% yield), which is then treated with hydrogen (4 atmospheres; room temperature) in glacial acetic acid and in the presence of palladium-based catalysts (5% on coal). After 3 hours of reaction, 1,1,3,3-tetramethylisoindoline is obtained (II, $R=CH_3$) with a yield of 96% (P. G. Griffiths, G. Moad, E. Rizzardo, D. H. Solomon, "Australian Journal of Chemistry" 1983, 36, 397).

More recently, international patent application PCT/EP2004/002071 describes a synthesis method which allows the preparation of tetra-alkylisoindolines:
- avoiding the use, in the Grignard reaction, of ethyl ether (an extremely flammable solvent which easily gives rise to the formation of peroxides which, in turn, carry the risk of explosion) or its mixtures; and
- effecting the subsequent hydrogenolysis of the product isolated from the previous step at atmospheric pressure, thus avoiding the use of equipment requiring high pressure operation for operating under pressure and simplifying the process.

Also in this case, however, there are a few problems mainly linked to the need of isolating the products after each of the four reaction steps, and in particular purifying the N-benzyl-1,1,3,3-tetra-alkylisoindolines, after the Grignard reaction, by chromatography on a basic alumina column, a procedure which (particularly on an industrial scale) is lengthy and costly, and the use of acetic acid which is corrosive, in the hydrogenolysis reaction (also using an extra chemical product in the general synthesis economy).

The Applicant has now found that it is possible to prepare stable nitrosylic radicals according to a much simpler process than those described so far and which solves the relative problems. In particular, this improved process allows:
- N-benzyl-1,1,3,3-tetra-alkylisoindolines to be obtained with a degree of purity which is sufficient for allowing them to be used in the subsequent passages without any purification (thus avoiding column chromatography);
- the above product to be obtained starting from simple and economical raw materials (an anhydride and an amine) with two successive reaction in a single step without having to isolate the product of the first reaction (N-benzylphthalimide) from the solution, but eliminating the water formed as by-product through an azeotropic distillation process, and using the solution thus obtained directly for the Grignard synthesis;
- the oxidation reaction to be effected directly on the alcoholic solution obtained from the hydrogenation, eliminating the need of acetic acid as solvent and an isolation and purification process of the 1,1,3,3-tetra-alkylisoindoline intermediate; and
- polymeric acids of molybdenum (or tungsten) to be used as catalysts in the oxidation with hydrogen peroxide, which as will appear more evident hereunder, are advantageous with respect to tungstates.

More specifically, according to this improved process, described in the enclosed claims, the stable nitroxyl radicals having formula (I) are prepared in two steps instead of four starting from phthalic anhydride and benzylamine. The first step takes place in an aromatic solvent, preferably toluene, in order to remove the reaction water by azeotropic distillation. The remaining solution of N-benzylphthalimide is directly transformed into N-benzyl-1,1,3,3-tetra-alkylisoindoline by treatment with a Grignard reagent prepared in methyl-tert-butyl ether, a less volatile solvent than ethyl ether (and therefore less subject to ignition) and which does not give rise to the formation of peroxides, starting from magnesium and a $C_1$-$C_4$ alkyl halide.

Either iodides, bromides or chlorides can be used as alkyl halides. They are normally used in an equimolar quantity with the magnesium or in the presence of an excess (generally up to 10%, but also from 3 to 9%) of either the one or the other reagent.

The molar ratio alkyl halide/N-benzylphthalimide can, in turn, range from 4 to 10 and can be optimized each time, depending on the greater or lesser reactivity of the halide selected and/or of the Grignard reagent deriving therefrom.

The best results are generally obtained with ratios ranging from 5 to 9.

The selection of the solvent is of particular importance. It is well known, in fact, that Grignard reagents must be prepared in ethers. If the reaction with N-benzylphthalimide is carried out in the presence of an ether, however, it is not completed but stops at intermediate products, mostly containing hydroxyl groups. It is therefore necessary to prepare the Grignard reagent in ether and then use it in another solvent with a higher boiling point (generally an aromatic solvent such as toluene, already used in the synthesis of N-benzylphthalimide). The ether can then be removed by distillation during the reaction which is thus completed to give the desired products. This need makes most of the ethers normally adopted for preparing Grignard reagents unusable, for example butyl ether ([n-$C_4H_9$]$_2$O with a boiling point of 142-143° C.) or butyl diglime ([n-$C_4H_9$O$CH_2CH_2$]$_2$O with a boiling point of 256° C.). Although tetrahydrofuran, is widely used for the preparation of Grignard reagents, surprisingly it gives low yields in the tetra-alkylation of N-benzylphthalimide. Methyl-tert-butyl ether, on the contrary, is an excellent solvent as, although it is much less volatile than ethyl ether, it has an acceptable boiling point (55-56° C.) and does not give rise to the formation of peroxides.

At the end of the reaction, a partial oxidation of the reaction mixture is effected with air. In order to obtain this partial oxidation, at the end of the Grignard reaction, n-hexane is added and the mixture is stirred in air from 3 to 5 hours. During this time, most of the impurities are oxidized giving rise to the formation of insoluble materials. At the same time, the colour of the suspended solids becomes dark purple, whereas the organic phase remains a pale-yellow colour. At the end, the raw reaction product is filtered, the filtrate is recovered and the solvents are removed at reduced pressure obtaining N-benzyl-1,1,3,3-tetra-alkylisoindoline having a purity which is such as to allow it to be used in the subsequent passages without further purification.

In the second step of the improved process, the N-benzyl-1,1,3,3-tetra-alkylisoindolines are transformed into 1,1,3,3-tetra-alkylisoindolines by treatment with hydrogen in alcohol, for example and preferably methanol, and in the presence of palladium-based catalysts at 5% by weight approximately on coal. It is preferable to operate at room temperature and atmospheric pressure. The solution is filtered to eliminate the catalyst and subjected to oxidation reaction with hydrogen peroxide in the presence of suitable catalysts and polar solvents, for example the same solvent as the second step (methanol) or possibly another solvent easily miscible therewith (water, acetonitrile, etc.) to give the final stable nitroxyl radical. As already mentioned, the prior art recommends the use of catalysts consisting of tungstates, but the Applicant has now found that the use of polymeric acids (or their salts) of molybdenum or tungsten provide various significant advantages. The characteristic of molybdenum and tungsten of producing a whole series of polymeric acids (polymolybdic and polytungstic) is well known, which can sometimes also incorporate different elements such as phosphorous, silicon, etc. (heteropolyacids). These acids and their salts of ammonium or alkaline metals are also capable of catalyzing the oxidation of 1,1,3,3-tetra-alkylisoindolines with hydrogen peroxide: it is in fact possible to use ammonium heptamolybdate [($NH_4$)$_6$$Mo_7O_{24}$·$4H_2O$], ammonium paratungstate [($NH_4$)$_{10}$$W_{12}O_{41}$], ammonium metatungstate [($NH_4$)$_6$$W_{12}O_{39}$·x $H_2O$] or tetra-alkylammonium peroxide phosphotungstates such as [(n-$C_8H_{17}$)$NCH_3$]$_3$$PW_4O_{24}$ (C. Venturello, R. D'Aloisio, "Journal of Organic Chemistry" 1988, 53, 1553). The use of polymolybdate salts is particular convenient: they are as efficient as tungstates but less costly and, in addition, their solutions in the presence of hydrogen peroxide are a dark orange colour which becomes yellowish when the concentration of hydrogen peroxide is negligible. This colour variation allows and easy and effective monitoring of the reaction trend.

According to the process improved by the Applicant, the oxidation of 1,1,3,3-tetra-alkylisoindolines with hydrogen peroxide is preferably carried out in polar solvents (for example water, methanol, acetonitrile or mixtures thereof), with temperatures which, in general, can range from 0 to 60° C. and atmospheric pressure. The duration of the reaction depends on the conditions adopted and, in particular, on the temperature, the nature and concentration of the substrate, the concentration of the hydrogen peroxide and the nature and quantity of catalyst.

If catalysts based on tungstates are used, the prior art suggests carrying out the reaction at room temperature for extremely long times, even 32 hours (P. G. Griffiths, G. Moad, E. Rizzardo, D. H. Solomon, "Australian Journal of Chemistry" 1983, 36, 397) or, with particular substrates, even 10 days (E. G. Rozantsev, V. D. Sholle, "Synthesis 1971, 190). The Applicant however has found that it is much more convenient to operate at moderate temperatures but higher than ambient values, preferably from 40 to 50° C. Under these conditions, the reaction is complete in much shorter times, normally ranging from 2 to 5 hours.

The concentration of the hydrogen peroxide used as oxidant is not critical: solutions of hydrogen peroxide (aqueous or in an organic solvent) can be used with concentrations ranging from 1 to 90%. The use of commercial aqueous solutions at 30% in such quantities that the hydrogen peroxide/substrate molar ratio ranges from 1.5 to 20, is particularly advantageous and safe. As previously specified, the duration of the reaction also depends on substrate/oxidation catalyst ratio. Expressing this ratio as:

(moles of substrate)/(gram-atoms of metal)

convenient durations are obtained with ratios ranging from 10 to 50.

The improved process for the preparation of stable nitroxyl radicals, object of the present invention, is now further described by means of the following example, provided for purely illustrative and non-limiting purposes.

EXAMPLE (Part A)

Toluene (250 cm$^3$) and phthalic anhydride (11.6 g, 78 mmoles) are charged into a reactor equipped with a Marcusson apparatus and benzylamine (8.4 g, 78 mmoles) is added dropwise. A gelatinous suspension is obtained and exothermy is observed (max 40° C.).

The mixture is heated to the boiling point of toluene, 110° C. and the reaction water is removed by means of azeotropic distillation. After 4 hours, the reaction is complete and the N-benzylphthalimide formed is completely in solution.

The solution previously obtained is used as such in the subsequent passage. Magnesium (8.75 g, 36.4 mmoles) and 20 cm$^3$ of methyl-tert-butylether are charged in an inert atmosphere. 2 drops of 1,2-dibromoethane are added and ethyl bromide (38.6 g, 356 mmoles) dissolved in methyl-tert-butylether (100 cm$^3$) is then added dropwise at such a rate to spontaneously maintain the reflux of the solvent. At the end of the addition, most of the methyl-tert-butylether is evaporated and the toluene solution of N-benzylphthalimide is added dropwise.

The temperature is brought to 110° C. After 4 hours the mixture is cooled to 20° C., hexane is added and the mixture is stirred in air for approximately 3-4 hours. In this way there is the selective precipitation of the impurities, visible as the precipitate becomes a purple colour and the organic phase a yellowish colour (at the end of the reaction it is a reddish-purple colour).

The raw mixture is filtered, the panel is washed with hexane, removing the solvents by distillation at reduce pressure. A product is obtained which is suitable for the subsequent passage which does not require a costly separation on a basic aluminum column. 9.34 g of 1,1,3,3-tetraethyl-2-benzyl-isoindoline are obtained (41%).

EXAMPLE (Part B)

The reaction is carried out in a glass reactor at room temperature and atmospheric pressure. 5% palladium on charcoal (1.7 g) is added to the solution of 1,1,3,3-tetraethyl-2-benzyl-isoindoline (9.34 g, 29.1 mmoles) in methanol (60 cm$^3$). After some vacuum/nitrogen cycles to eliminate the oxygen, hydrogen is charged. After 3 hours the catalyst is filtered on paper and the solution is used as such for the subsequent oxidation (the yield of 1,1,3,3-tetraethyl-isoindoline is 93% by GC).

The following products are charged into a flask in order:
6.6 g (28.5 mmoles) of 1,1,3,3-tetraethylisoindoline in 60 ml of methanol;
3.7 ml of acetonitrile;
1.87 g (22 mmoles) of sodium bicarbonate;
180 mg (0.146 mmoles equal to 1 mmole of Mo) of ammonium heptamolybdate [$(NH_4)_6Mo_7O_{24}\cdot 4H_2O$];
10.5 ml (92.6 mmoles) of hydrogen peroxide 30% w/v; and the mixture is stirred at 45° C. for 2 h.

After adding a saturated aqueous solution of sodium chloride, the product is extracted with ethyl ether, the organic extract is washed with water until it becomes neutral and anhydrified on sodium sulfate. The solvent is removed by distillation at reduced pressure.

The product obtained, having a solid appearance and orange colour, has a purity of at least 90% and is suitable for polymerization. 4.98 g of 1,1,3,3-tetraethylisoindolin-2-yloxyl are obtained (yield 71%).

The invention claimed is:
1. A process for the preparation of stable nitroxyl radicals having the general formula (I),

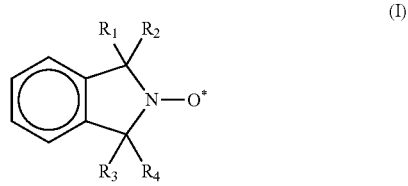

(I)

wherein $R_1$, $R_2$, $R_3$ and $R_4$, the same or different, represent alkyl or isoalkyl groups containing from 1 to 8 carbon atoms, which comprises:
 a. preparing a first intermediate N-benzylphthalimide starting from phthalic anhydride and benzylamine by reaction in an aromatic solvent, and removing the reaction water by means of azeotropic distillation;
 b. transforming the N-benzylphthalimide, in the same aromatic solvent, into N-benzyl-1,1,3,3-tetra-alkylisoindoline by treatment with a Grignard reagent prepared in methyl-tert-butyl ether starting from magnesium and a $C_1$-$C_4$ alkyl halide;
 c. continuously distilling the methyl-tert-butyl ether solvent during the reaction;
 d. purifying the reaction mixture, by oxidation with air, stirring the same for times ranging from 3 to 5 hours and filtering the raw reaction product thus obtained;
 e. subjecting the purified intermediate N-benzyl-1,1,3,3-tetra-alkylisoindoline obtained from step (d) to a hydrogenolysis reaction in methanol, in the presence of hydrogen and a supported palladium catalyst, at room temperature and atmospheric pressure; and
 f. subjecting the hydrogenolysis product of step (e) to an oxidation reaction in a polar solvent compatible with methanol, with hydrogen peroxide in the presence of a catalyst selected from polymolybdic and polytungstic acids or salts, optionally incorporating an element selected from phosphorous or silicon.

2. The process according to claim 1, wherein the alkyl halide is used in an excess of up to 10% with respect to the magnesium.

3. The process according to claim 1, wherein the magnesium is used in an excess of up to 10% with respect to the alkyl halide.

4. The process according to claim 1, wherein the alkyl halide/N-benzylphthalimide molar ratio in step (b) ranges from 4 to 10.

5. The process according to claim 1, wherein the solvent of steps (a) and (b) is toluene.

6. The process according to claim 5, wherein the synthesis of benzylphthalimide, the azeotropic distillation and subsequent reaction with the Grignard reagent are effected in the same reactor.

7. The process according to claim 1, wherein the hydrogenolysis catalyst consists of 3-6% by weight of palladium on charcoal.

8. The process according to claim 1, wherein the polymolybdic and polytungstic salts are selected from those of ammonium or alkaline metals.

9. The process according to claim 1, wherein the oxidation reaction is carried out in methanol, water or acetonitrile.

10. The process according to claim 1, wherein the oxidation reaction is carried out at a temperature ranging from 40 to 50° C.

11. The process according to claim 1, wherein the concentration and quantity of hydrogen peroxide are such as to give a H2O2/substrate molar ratio ranging from 1.5 to 20.

12. The process according to claim 1, wherein the ratio: moles of substrate/gram-atoms of metal of oxidation catalyst, ranges from 10 to 50.

13. The process according to claim 1, wherein the hydrogenolysis solvent is methanol and the resulting solution, after filtration, is used directly in the oxidation reaction.

14. The process according to claim 1, wherein step f). the hydrogenolysis product is subjected to an oxidation reaction with hydrogen peroxide in the presence of at least one of an ammonium heptamolybdate, an ammonium paratungstate, an ammonium metatungstate and a tetra-alkyl ammonium ammonium peroxide phosphotungstate.

15. The process according to claim 1, wherein the hydrogenolysis product is subjected to an oxidation reaction with hydrogen peroxide at a temperature of from 40 to 50° C. for from 2 to 5 hours.

16. The process according to claim 1, where $R_1$, $R_2$, $R_3$, and $R_4$ are each ethyl groups.

17. The process according to claim 1, wherein the hydrogenolysis reaction is carried out in the presence of a palladium catalyst supported on charcoal.

18. The process according to claim 1, further comprising: reacting the oxidation product of step f)., as an intermediate to form a complex molecule.

19. The process according to claim 1, further comprising: inhibiting a polymerization a monomer mixture by mixing the oxidation reaction product of step f). with the monomer mixture.

* * * * *